United States Patent [19]

Benz

[11] Patent Number: 4,544,816

[45] Date of Patent: Oct. 1, 1985

[54] SWITCHING ARRANGEMENT FOR A ROTATING TOOTHBRUSH

[76] Inventor: Dieter Benz, Hirschstrasse 21, D-7900 Ulm, Fed. Rep. of Germany

[21] Appl. No.: 551,821

[22] Filed: Nov. 10, 1983

[30] Foreign Application Priority Data

Mar. 16, 1983 [DE] Fed. Rep. of Germany ....... 3309412

[51] Int. Cl.⁴ .................. A46B 9/04; A46B 13/02; H01H 29/20; H01H 35/02
[52] U.S. Cl. ..................... 200/52 R; 15/23; 200/1 V; 200/61.52
[58] Field of Search ............... 200/52 R, 61.47, 61.52, 200/61.83, 182, 183, 220, 224, 225; 15/23

[56] References Cited

U.S. PATENT DOCUMENTS

| 3,846,748 | 11/1974 | Hopwood | 200/61.47 X |
| 4,163,300 | 8/1979 | Quint | 200/61.52 X |
| 4,275,749 | 6/1981 | Caroli | 15/23 X |

FOREIGN PATENT DOCUMENTS 3211984 12/1982 Fed. Rep. of Germany .

Primary Examiner—J. R. Scott
Attorney, Agent, or Firm—Michael J. Striker

[57] ABSTRACT

A switching arrangement for a rotating toothbrush which includes a rectangular casing accommodating the electric motor has a gravity switch provided in the housing and a switch actuated manually and provided externally on the housing. As a mercury gravity switch, a sensor is used, which consists of a tube closed at each end thereof and provided with a respective bottom portion at each end. Through each of the bottom portions at a lateral location, a conductor wire projects wherein through one of the bottom portions a further conductor wire projects whose forward portion within the tube is arranged at a distance to the wall of the tube and extends parallel to the conductor wires and leads almost to the end of the other bottom portion.

31 Claims, 4 Drawing Figures

SWITCHING ARRANGEMENT FOR A ROTATING TOOTHBRUSH

BACKGROUND OF THE INVENTION

The invention relates to a switching arrangement for rotating toothbrush.

It is known to provide a toothbrush which includes a rectangular housing in which an electromotor is arranged. Via a shaft, the motor drives a clutch shaft carrying the toothbrush wherein the housing accommodates a mercury gravity switch for reversing the direction of rotation of the motor. Furthermore, a manually actuatable switch is arranged outside the housing which provides a reversing of the rotational direction of the motor for treating the upper and lower jaw, wherein the reversing of the rotational direction of the electromotor for the treatment of the inner and outer side of the tooth is obtained through turning of the toothbrush around the longitudinal axis.

A rotating toothbrush with such an unconfusable switching arrangement is described in West German patent document 3,211,984. Through the one time operation of the manually actuatable switch, it is determined at the start of the tooth brushing whether the brushing should start with the teeth of the upper or the lower jaw. After this determination and the start of the brushing, the reversing for the right and left sides for the inner and outer side of the tooth is automatically obtained so that the brush provides continuously the correct rotational direction i.e., from the gums to the tooth that is from "red" to "white". For adjusting the correct rotational direction for the other part of the jaw, the switch is manually actuated so that the device is programmed for brushing the other half of the jaw. A correct switching of the manually actuatable switch can be confirmed by an optical indication or be obtained by sensing means or accoustic means or by any combination of these means. For left-handers, these indicating means are arranged in the opposite manner.

With the switching arrangement of the known rotating toothbrush, it is achieved effectively for the first time to control the non-interchangeability of the rotational directions by simple means.

A problem of all known rotating toothbrushes operating with a centrifugal switch resides in the duration of the reversing and above all in the response sensitivity upon tilting of the switch. With the switches used so far, a so-called "stammering" i.e., a momentary, frequent stopping of the rotational movement of the motor cannot be prevented upon rotation of the toothbrush along the longitudinal axis when the switching elements of the switch, disengaged from the contact and seek to engage the counter contact. The stammering impairs, however, the brushing of the teeth in a considerable manner because it cannot be recognized whether the toothbrush stammers or stops is caused by the switching process or by of a defect. Moreover, upon stammering of the toothbrush, the rotational direction can be altered so that even incorrect rotational directions (white to red) can occur.

SUMMARY OF THE INVENTION

It is a general object of the present invention to avoid the prior art disadvantages.

In general, it is an object of the present invention to provide a switching arrangement for a rotating toothbrush which provides a flowing reversing of the rotational directions and avoids a stammering of the tooth brush.

A concomitant object of the present invention is to provide a switching arrangement which is simple in construction, reliable in operation and inexpensive nevertheless.

In keeping with these objects and with others which will become apparent hereinafter, one feature of the present invention resides, briefly stated, in a switching arrangement which comprises at least one sensor provided as a gravity switch and including a tube defining a closed interior and having two opposing bottom portions in longitudinal direction of the tube, each of the bottom portions being arranged at a respective end of the tube, a first conductor wire having a forward portion projecting into the interior of the tube to one of the bottom portions, a second conductor wire having a forward portion projecting into the interior of the tube through the other of the bottom portions and being arranged at a distance to the first conductor wire, a third conductor wire having a forward portion projecting into the interior of the tube through one of the bottom portions at a distance to the first and second conductor wires and extending almost to the other of the bottom portions, and a mercury bead located in the interior of the tube for reversing the direction of rotation of the motor in dependence on the position of the toothbrush.

Preferably, two such sensors are provided and connected to an electric energy source wherein the third conductor wire of one of the sensors is connected to the positive pole of the energy source and the third conductor wire of the other of the sensors is connected to the negative pole of the energy source.

With the provision of such a switching arrangement for a rotating toothbrush, a stammering upon changing the rotational direction is prevented so that the brushing process is not impaired.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
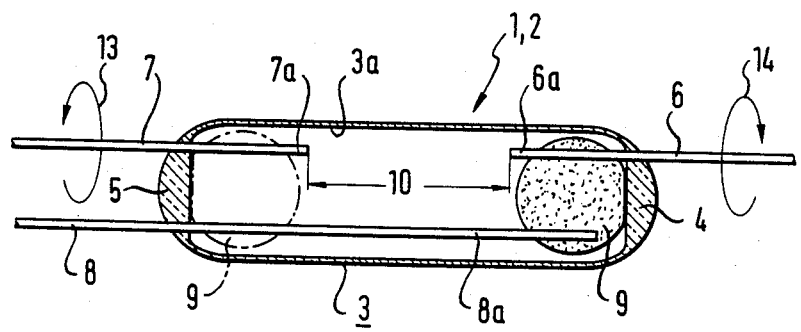
FIG. 1 is a schematic side view of a switching arrangement according to the invention.

The switching arrangement according to the invention is provided with several, preferably two correspondingly formed sensors 1, 2. The sensor 1, 2 which is especially shown in FIG. 1 includes a tube 3 which is closed at its both ends and has preferably a circular cross-section. The tube 3 is made of glass or synthetic material and is preferably provided with outwardly curved bottom portions 4, 5. Projecting through the bottom portion 4 at a lateral, that is eccentrical location is the forward portion 6a of a conductor wire 6. The forward portion 6a extends parallel into the tube 3, however, at a distance thereto and does not reach to the center of the tube as can be seen from FIG. 1. In the same manner, the forward portion 7a of a conductor wire 7 projects through the bottom portion 5. Preferably, the conductor wire 7 is arranged opposite to the conductor wire 6 in longitudinal direction of the tube and the forward portion 6a is preferably of same length as the forward portion 7a.

As can be further seen from FIG. 1, a third conductor wire 8 projects with its forward portion 8a to the bottom portion 5 wherein the forward portion 8a is arranged within the tube 3 at a distance to the wall 3a and extends parallel to the conductor wire 7. The conductor wire 8 is longer than the conductor wire 7 so that the forward portion 8a projects partly above the forward portion 6a and ends shortly before the bottom portion 4.

Within the tube 3, there is located a mercury bead 9 whose diameter is preferably slightly smaller than the diameter of the tube 3 and wherein the length of the tube 3 is for example approximately the quadruple of the diameter of the mercury bead 9. Moreover, the distance 10 between the conductor wires 6, 7 is larger, preferably twofold of the diameter of the mercury bead 9. The vertical distance within the tube 3 between the conductor wire 8 and the respective forward portion 6a, 7a of the conductor wire 6, 7 is smaller than the diameter of the mercury bead 9.

Outside the tube 3, the conductor wire 8 is connected to an electric energy source 11, e.g. a battery or an accumulator. The conductor wires 6, 7 are in communication with a drive motor 12 in such a manner that the motor rotates in direction of arrow 13 when the mercury bead 9 is located at the left hand in FIG. 1 and rotates in direction of arrow 14 when the mercury bead 9 is located at the right hand in FIG. 1.

Figure 2:
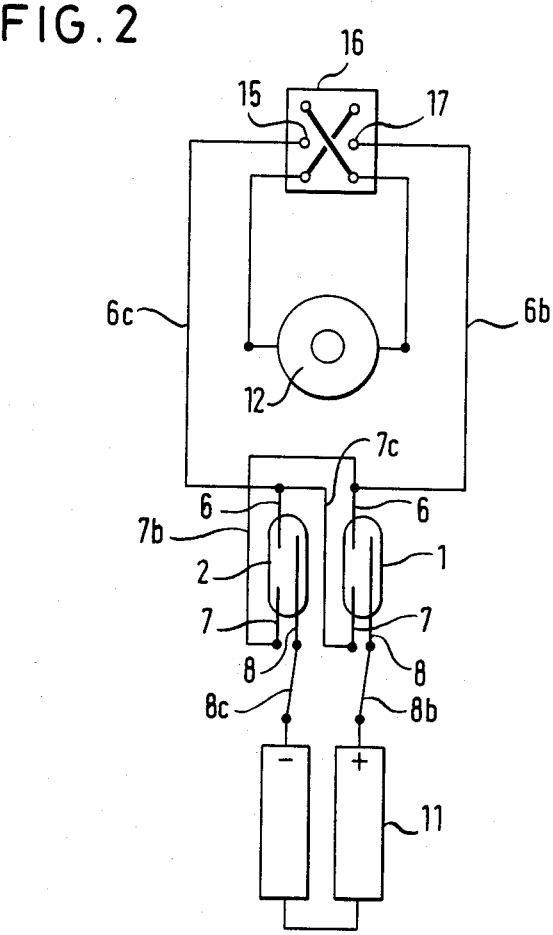
FIG. 2 is schematically the switching arrangement according to the invention provided with two sensors.

According to the invention, preferably two sensors 1, 2 are used according to FIG. 2. In this embodiment, for example the conductor wire 8 of the sensor 1 is in communication with the positive pole of the electric energy source 11 via a line 8b and the conductor wire 8 of the sensor 2 is in communication with the negative pole of the electric energy source 11 via a line 8c. In addition, the conductor wire 7 of the sensor 2 is connected with the conductor wire 6 of the sensor 1 via a line 7b while the conductor wire 7 of sensor 1 is connected to the conductor wire 6 of the sensor 2 via a line 17. The conductor wire 6 of the sensor 2 is connected via a line 6c with a pole 15 of a manually actuatable switch 16 while the conductor wire 6 of the sensor 1 is connected via a line 6d with the counter pole 17 of the switch 16. The switching paths of the switch 16 are developed in such a manner that upon actuation of the switch a clockwise rotation or counterclockwise rotation of the switch can be chosen.

Through the inventive combination of two sensors, a stammering-free run of the toothbrush is secured upon reversing of the rotational direction of the motor wherein especially the forward portion 8a of the conductor wire 8 causes that each mercury bead 9 of the sensors 1, 2 is continuously in contact with one of the poles of the energy source 11 that is the mercury bead of sensor 1 with the positive pole and the mercury bead of the sensor 2 with the negative pole so that the reversing is obtained in a "flowing" manner.

Figure 3:
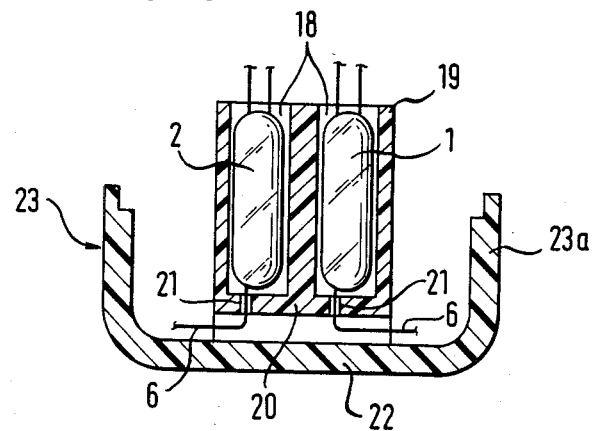
FIG. 3 illustrates schematically the provision of the switching arrangement within a housing shell of the toothbrush housing in a cross-sectional view.
Figure 4:
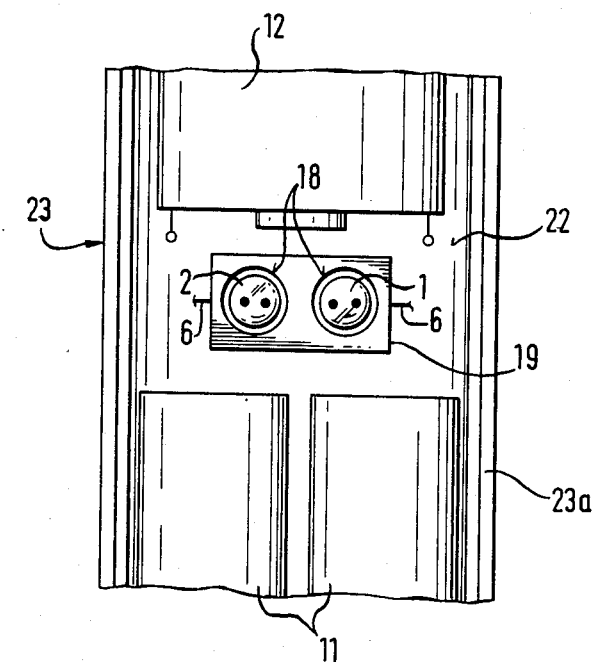
FIG. 4 is a schematic top view of the switching arrangement provided in the housing shell.

According to a preferred embodiment of the invention, the sensors 1, 2 are arranged preferably in a form- and force-locking manner in two chambers 18 which are open at their top portion and arranged parallel to each other. The chambers 18 are part of a housing 19 preferably of synthetic material wherein each chamber 18 has a bottom portion 20 provided with breakthroughs for the conductor wires, e.g. for the conductor wire 6 (FIG. 3). The housing 19 is arranged on the bottom 22 of a housing shell 23 which forms one part of the casing of the toothbrush (not completely shown). Each of the housing shells 23 are U-shaped in cross-section. The housing 19 is provided in the housing shell 23 in such a manner that the sensors 1, 2 are arranged side by side in transverse direction of the toothbrush casing preferably vertical to the longitudinal axis (FIGS. 3, 4). In this embodiment, the electric energy source 11 is preferably arranged to the rear area of the toothbrush casing behind the sensor housing 19 and the motor 12 is arranged before the sensor housing 19 (FIG. 4).

The housing shell 23 is closed by a further housing shell (not shown) which is also of U-shaped cross-section so as to form the casing of the toothbrush. Consequently, a rectangular casing is obtained which structure is preferred because it supports the non-interchangeability and the prevention of the stammering of the toothbrush. This is due to the fact that with a rectangular casing, the position of the sensors 1, 2 can be determined by providing the manually actuatable switch external on the side wall 23a and by marking the sides of the toothbrush which is to be inserted into the mouth facing the teeth so that an exactly controllable rotation of the toothbrush housing around 180° around its longitudinal axis can be performed in order to obtain a stammering-free reversing of the motor and consequently for changing the rotational direction of the toothbrush.

It will be understood that each of the elements described above, or two or more together, may also find a useful application in other types of switching arrangements for a rotating toothbrush, differing from the types described above.

While the invention has been illustrated and described as embodied in a switching arrangement for a rotating toothbrush, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A switching arrangement for a rotating toothbrush having a casing and being driven by a motor accommodated within the casing, the arrangement comprising:
    two sensors provided as a gravity switch each including a tube defining a closed interior and having an inner diameter and two opposing bottom portions in longitudinal direction of the tube, each of the bottom portions being arranged at a respective end of the tube; a first conductor wire having a forward portion projecting into the interior of the tube through one of the bottom portions; a second conductor wire having a foward portion projecting into the interior of the tube through the other of the bottom portions and being arranged at a distance to the first conductor wire; a third conductor wire having a forward portion projecting into the interior of the tube through one of the bottom portions at a distance to the first and second conductor wires and extending almost to the other of the bottom portions; and a mercury bead located in the interior of the tube and having a diameter smaller than the inner diameter of the tube for reversing the direction of rotation of the motor in dependence on the position of the toothbrush.

2. An arrangement as defined in claim 1, wherein the tube is of a circular cross-section.

3. An arrangement as defined in claim 1, wherein the tube is of glass.

4. An arrangement as defined in claim 1, wherein the tube is of a synthetic material.

5. An arrangement as defined in claim 1, wherein each of the bottom portions is outwardly curved.

6. An arrangement as defined in claim 1, wherein the forward portions of the first and second conductor wires extend eccentrically into the interior of the tube.

7. An arrangement as defined in claim 1, wherein the tube is defined by a wall and has a center, the forward portions of the first and second conductor wires being arranged parallel at a distance to the wall and extending at a distance to the center.

8. An arrangement as defined in claim 1, wherein the forward portions of the first and second conductor wires oppose each other in longitudinal direction of the tube.

9. An arrangement as defined in claim 1, wherein the forward portions of the first and second conductor wires are of an equal length.

10. An arrangement as defined in claim 1, wherein the forward portion of the third conductor wire extends parallel to the forward portions of the first and second conductor wires.

11. An arrangement as defined in claim 1, wherein the forward portion of the third conductor wire is longer than the forward portion of the first and second conductor wires.

12. An arrangement as defined in claim 1, wherein the mercury bead has a diameter, the tube having a length correpsonding to a multiple of the diameter of the mercury bead.

13. An arrangement as defined in claim 12, wherein the length of a tube is quadruple of the diameter of the mercury bead.

14. An arrangement as defined in claim 1, wherein the mercurcy bead has a diameter, the distance between the forward portions of the first and second conductor wires being larger than the diameter of the mercury bead.

15. An arrangement as defined in claim 14, wherein the distance between the forward portions of the first and second conductor wires is double the diameter of the mercury bead.

16. An arrangement as defined in claim 1, wherein the mercury bead has a diameter, the vertical distance between the forward portion of the third conductor wire and the forward portions of the first and second conductor wires being smaller than the diameter of the mercury bead.

17. An arrangement as defined in claim 1; and further comprising a housing having two chambers provided with open upper portions and arranged parallel to each other for accommodating the sensors.

18. An arrangement as defined in claim 17, wherein the housing is of a synthetic material.

19. An arrangement as defined in claim 17, wherein the sensors are accommodated in the housings in a form- and force-locking manner.

20. An arrangement as defined in claim 17, wherein the chambers have a bottom provided with a breakthrough for the associated conductor wire.

21. An arrangement as defined in claim 17; and further comprising a housing shell forming a part of the casing of the toothbrush and having a bottom, the housing being located on the bottom of the housing shell.

22. An arrangement as defined in claim 21, wherein the housing shell has a U-shaped cross-section.

23. An arrangement as defined in claim 22; and further comprising a second such housing shell forming another part of the casing so that upon connecting the first housing shell and the second housing shell, the casing is of a rectangular cross-section.

24. An arrangement as defined in claim 21; wherein the first and second sensors being arranged side by side in transverse direction of the casing.

25. An arrangement as defined in claim 24, wherein the casing has a longitudinal axis, the first and second sensors being arranged vertical to the longitudinal axis.

26. An arrangement as defined in claim 17; and further comprising an energy source for the sensor, the casing having a rear portion accommodating the energy source in a location behind the housing and the motor being located in front of the housing.

27. A switching arrangement for a rotating toothbrush having a casing and being driven by a motor accommodated within the casing, the arrangement comprising:

two sensors provided as a gravity switch each including a tube defining a closed interior and having an inner diameter and two opposing bottom portions in longitudinal direction of the tube, each of the bottom portions being arranged at a respective end of the tube; a first conductor wire having a forward portion projecting into the interior of the tube through one of the bottom portions; a second conductor wire having a forward portion projecting into the interior of the tube through the other of the bottom portions and being arranged at a distance to the first conductor wire; a third conductor wire having a forward portion projecting into the interior of the tube through one of the bottom portions at a distance to the first and second conductor wires and extending almost to the other of the bottom portions; a mercury bead located in the interior of the tube and having a diameter smaller than the inner diameter of the tube for reversing in a stammer-free manner the direction of rotation of the motor by making electrical contact between the third conductor and, alternately, the first conductor and the second conductor in dependence on the position of the toothbrush; and an electric energy source having a positive pole and a negative pole, the third conductor wire of one of the sensors being connected to the positive pole of the energy source, and the third conductor wire of the other of the sensors being connected to the negative pole of the energy source.

28. An arrangement as defined in claim 27, wherein the second conductor wire of one of the sensors is connected to the first conductor wire of the other of the sensors, and the first conductor wire of the one of the sensors is connected to the second conductor wire of the other of the sensors.

29. An arrangement as defined in claim 27; and further comprising a manually actuatable switch having two poles, the first conductor wire of one of the sensors being connected to one of the poles of the switch and first conductor wire of the other of the sensors being connected to the other of the poles of the switch.

30. An arrangement as defined in claim 29, wherein the casing has a side wall, the switch being arranged externally from the side walls.

31. An arrangement as defined in claim 30, wherein the side wall is arranged so as to face the teeth.

* * * * *